United States Patent
Weightman et al.

(10) Patent No.: US 6,482,430 B1
(45) Date of Patent: Nov. 19, 2002

(54) IMPROVEMENTS RELATING TO BRAN GELS

(75) Inventors: Richard Mark Weightman, Huntingdon (GB); Colin Stanley Fitchett, Cambridge (GB); Roderick Greenshields, Swansea (GB)

(73) Assignee: Cambridge Biopolymers Limited, Cambridgeshire (GB)

( * ) Notice: Subject to any disclaimer, the term of this patent is extended or adjusted under 35 U.S.C. 154(b) by 0 days.

(21) Appl. No.: 09/044,726

(22) Filed: Mar. 19, 1998

(30) Foreign Application Priority Data

Mar. 20, 1997 (GB) ............................... 9705739
Aug. 28, 1997 (GB) ............................... 9718071

(51) Int. Cl.⁷ .................. A61K 47/00; A61K 9/68; A23L 1/05
(52) U.S. Cl. ............. 424/441; 424/439; 424/440; 426/573
(58) Field of Search ................ 426/618, 425, 426/436, 573; 424/440, 441

(56) References Cited

U.S. PATENT DOCUMENTS

| | | | | |
|---|---|---|---|---|
| 4,961,937 A | * | 10/1990 | Rudel | ............. 426/19 |
| 5,530,112 A | * | 6/1996 | Greenshields et al. | ... 526/123.1 |
| 5,633,032 A | * | 5/1997 | Greenshields et al. | ...... 426/618 |
| 5,989,598 A | * | 11/1999 | Whalen | ........... 426/28 |

FOREIGN PATENT DOCUMENTS

| | | | | |
|---|---|---|---|---|
| DD | 249 627 | 9/1987 | ............. | A23D/5/00 |
| DD | 266 960 | 4/1989 | ............. | A23J/1/12 |
| EP | 0 521 707 | 1/1993 | ......... | A23L/1/0534 |
| FR | 2 545 101 A1 | 4/1983 | | |
| FR | 2 545 101 A1 | 11/1984 | | |
| GB | 2 261 671 | 5/1993 | ........... | C08B/37/14 |
| WO | WO 93/10157 | 5/1993 | ............. | C08B/3/14 |
| WO | 93/10157 | * 5/1993 | ............. | C08B/3/14 |
| WO | WO 93/10158 | 5/1993 | ............. | C08B/37/14 |
| WO | WO 96/03440 | 2/1996 | ........... | C08B/37/00 |

OTHER PUBLICATIONS

J. F. Thibault et al., "Gelatin of Sugar Beet Pectin by Oxidative Coupling", in *The Chemistry and Technology of Pectin*, Reginald H. Walter, editor, Chapter 7, 119–133, Academic Press, Inc.,1991.

R. C. Hoseney et al., "A Mechanism for the Oxidative Gelation of Wheat Flour Water–Soluble Pentosans", *Cereal Chemistry*, 58(5), 421–439, 1981.

J. Michniewicz, et al., "Water–Insoluble Pentosans of Wheat:Composition and Some Physical Properties", *Cereal Chemistry*, 67(5), 434–439, 1990.

T. Geissman et al., "On the Composition of the Water Soluble Wheat Flour Pentosans and their Oxidative Gelation", *Lebensmittel Wissenschaft Und Technologie*, 6, 59–62, 1973.

Abstract: XP–002070595 & JP 01 062 303 A with translation.

Abstract: XP–002070596 & JP 02 001 701 A with translation.

Abstract: XP–002070597 & JP 58 041 824 A with translation.

* cited by examiner

*Primary Examiner*—Russell Travers
*Assistant Examiner*—Shengjun Wang
(74) *Attorney, Agent, or Firm*—Heller Ehrman White & McAuliffe

(57) ABSTRACT

Hemicellulosic cereal extracts suitable as substrates for oxidative gelation, gels prepared therefrom, processes for their production, products containing such gels and applications thereof. Preferred sources are wheat sources, when the preparative process may involve the removal of contaminating proteins.

2 Claims, 1 Drawing Sheet

FIGURE 1 EXTRACTION OF SUPERGEL FROM WHEAT BRAN
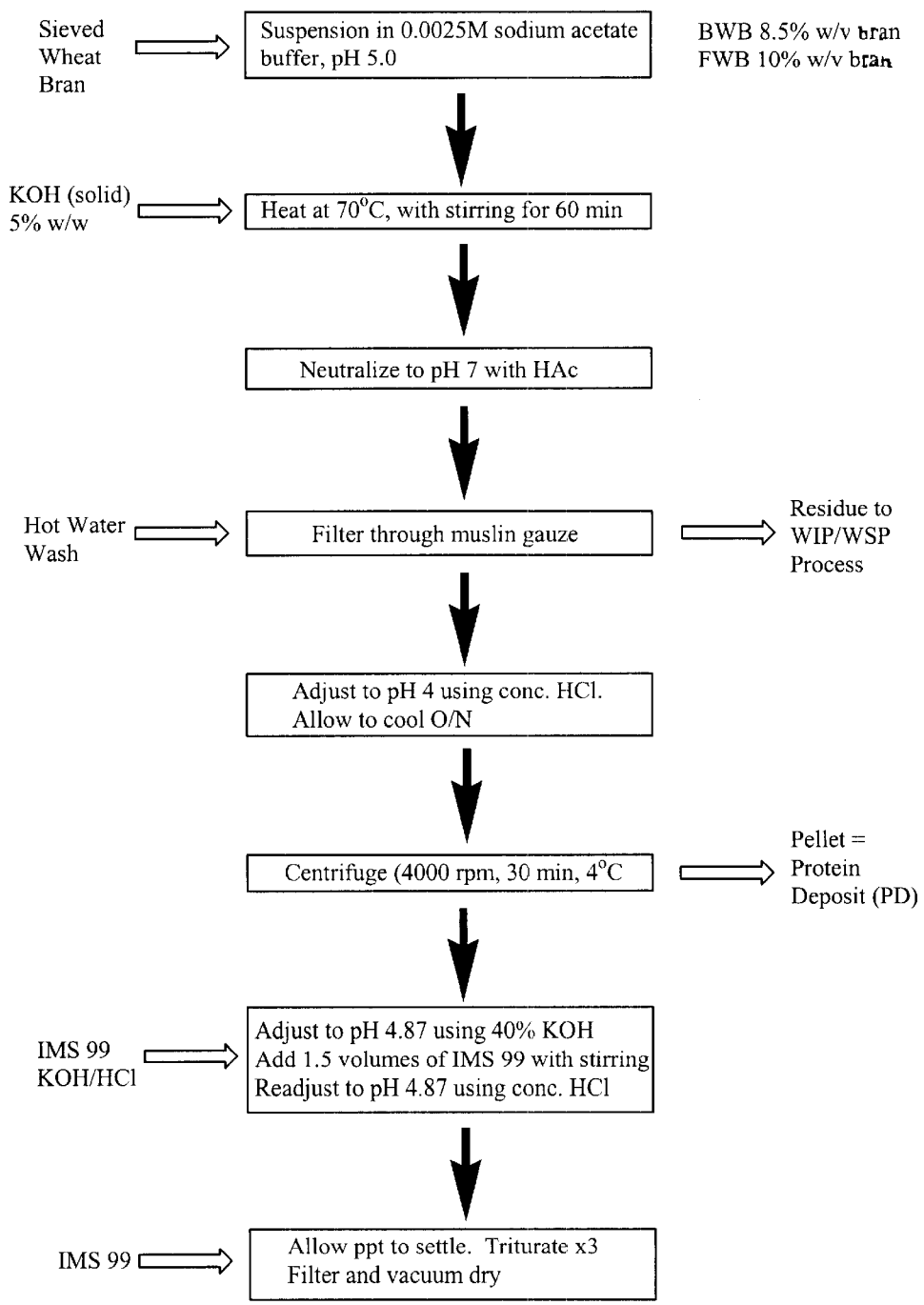

IMPROVEMENTS RELATING TO BRAN GELS

This application claims foreign priority of GB 9705739.2 titled Aug. 28, 1997, and GB 970579.2 titled Mar. 20, 1997.

The present invention relates to hemicellulosic cereal extracts suitable as substrates for oxidative gelation ("gelling hemicelluloses"), to gels prepared therefrom, to processes for their production, to products containing such gels and to various applications thereof. In particular, the present invention relates to an improved process for preparing gelling hemicelluloses from cereals (especially wheat).

The term "hemicellulose" and "hemicellulosic material" are terms of art used to embrace non-cellulosic, non-starch plant polysaccharides. The term therefore embraces inter alia pentosans, pectins and gums.

Some hemicelluloses are suitable as substrates for oxidative gelation ("gelling hemicelluloses"): such hemicelluloses often have substituents with phenolic groups which are cross-linkable with certain oxidizing agents.

Arabinoxylan and pectin constitute two particularly important classes of hemicellulose. Arabinoxylans consist predominantly of the pentoses arabinose and xylose, and are therefore often classified as pentosans. However, in many cases hexoses and hexuronic acid are present as minor constituents, and therefore they may also be referred to descriptively as heteroxylans.

The arabinoxylan molecule consists of a linear backbone of (1–4(-β-xylopyranosyl units, to which substituents are attached through 02 and 03 atoms of the xlosyl residues. The major substituents are single α-L-arabinofuranosyl residues. Single α-D-glucoronopyranosyl residues and their 4-O-methyl ethers are also common substituents.

Arabinoxylan preparations are usually heterogeneous with respect to the ratio of xylose to arabinose (i.e. the degree of substitution) and in the pattern of substitution of the arabinosyl units along the (1–4)-β- xylan backbone.

Phenolic acid including ferulic acid) and acetyl substituents occur at intervals along the arabinoxylan chains. These substituents to some extent determine the solubility of the arabinoxylan. Arabinoxylan preparations bearing phenolic (e.g. ferulic acid substituents) are referred to herein as "AXE", while those bearing acetyl substituents are designated "AXA". Similarly, preparation bearing both phenolic (e.g. ferulic acid, and acetyl substituents are hereinafter abbreviated to the designation "AXFA". Arabinoxylan preparations having few phenolic (e.g. ferulic acid, substituents are designated "AX": when the degree of substitution falls below that required for oxidative gelation, the arabinoxylan is designated a "non-gelling arabinoxylan" (a term which therefore embraces AX and AXA).

Pectins constitute another important class of hemicelluloses. As used herein and unless otherwise indicated, the term "pectin" is used sensu lato to define hemicellulose polymers rich in D-galacturonic acid. Many (but not all) are cell wall components. The term "pectin" is also used herein sensu stricto to define the so-called "true pectins", which are characterized by the presence of an O-(α-D-galacturonopyranosyl)-(1–2)-L-rhamnopyranosyl linkage within the molecule.

The pectins may be subcatergorized on the basis of their structural complexity. At one extreme are "simple pectins", which are galacturonans. At the other extreme are "complex pectins" exemplified by rhamnogalacturonan II, which contains at least 10 different monosaccharide components in the main chain or as a components of branches. Pectins of intermediate complexity (herein referred to as "mesocomplex pectins" contain alternate rhamnose and galacturonic acid units, while others have branches of glucoronic acid linked to galacturnoic acid.

Complex and mesocomplex pectins are made up of "smooth" regions (based on linear homogalacturonan) and "hairy" regions corresponding to the rhamnogalacturonan backbone with side-branches of varying length.

Certain pectins (for example, pectins obtainable from representatives of the plant family Chenopodiaceae, which include beets (e.g. sugar beet), spinach and mangelwurzels) are substituted to some extent with substituents derived from carboxylic acids (usually substituted cinnamic acids) containing phenolic groups. Such pectins may be oxidatively cross-linked to produce viscous solutions or gels via their phenolic substituents. This can be achieved by powerful oxidants (e.g. persulfate - see J. - F. Thibault et alia, in *The Chemistry and Technology of Pectin,* Academic Press 1991, Chapter 7, pages 119–133) or a combination of peroxidase and hydrogen peroxide (see Thibault et alia, ibidem). Fr 2 545 101 Al also describes the gelling of beet pectins using an oxidant (e.g. hydrogen peroxide) and an enzyme (peroxidase). Such pectins are referred to herein as "gelling pectins".

Sugar beet pectin is especially rich in arabinan. Arabinan contains β-1,5-linked arabinose in the backbone with α-(1–>3) or α-(1–>2)-linked arabinose residues, whereas arabinogalactan contains β-1,4-linked galactose in the backbone, with α-(1–>3) or a α-(1–>2) linked arabinose residues. Ferulyl substituents are linked to the arabinose and/or the galactose in the arabinan and arabinogalactan side-branches of the rhamnogalacturonan part. The "ferulic acid" content varies according to the extraction method, but is often about 0.6%.

Beet pectins obtained by processes which partially remove arabinose residues may exhibit improved gelling properties. Thus, procedures involving mild acid treatment and/or treatment with an α-arabinofuranosidase will improve the gelling properties of the pectin (see F. Guillon et alia ibidem). Such pectins are hereinafter referred to as "treated pectins".

It has long been known that certain flour extracts (e.g. wheat and rye flour extracts) can form gels in the presence of certain oxidants (e.g. upon the addition of hydrogen peroxide). The phenomenon is known in the art as "oxidative gelation", and an extensive literature exists on the subject of oxidative gelation of wheat flour extracts. According to the literature, the gels arise as high molecular weight arabinoxylan and protein molecules become inter- and/or intra-linked (via inter alia diferulate bridges) - see e.g. Hoseney and Fabuion (1981), Cereal Chem., 58: 421.

Most of the work in this area has focused on water soluble pentosans from wheat flour. In these studies, wheat flour is extracted with water (usually at room temperature) to yield gelling arabinoxylans. However, water-insoluble wheat pentosans extracted from wheat flours with various concentrations of cold sodium hydroxide have also been shown to form gels (Michniewicz et alia, Cereal Chemistry 67(5): 434–439 (1990).

WO 93/1058 describes the preparation of hemicellulosic material from various brans and the oxidative gelation of maize-derived hemicelluloses using an oxidizing system comprising a peroxide, (such as hydrogen peroxide) and an oxygenase (such as a peroxidase). The hemicellulosic material for use as a gelling agent is prepared by hot water or mild alkali extraction.

However, gelling hemicelluloses from some cereal sources (including wheat) produced by known processes form gels which are unsatisfactory for many uses. Such gels are generally opaque, relatively soft, pigmented and exhibit marked syneresis on storage. These properties limit their utility in many potential fields of application (including food technology and the pharmaceutical industry).

There is therefore a need for improved methods of producing gelling hemicelluloses from testaceous cereal fractions (e.g. cereal brans) which exhibit improved gelling characteristics and which do not exhibit these undesirable properties.

It has now been discovered that the undesirable characteristics of the gels produced from certain hemicellulosic bran extracts arise from the presence of contaminating proteins. In certain brans (e.g. many what brans and other bran sources which contain residual endosperm material), such proteins are present at concentrations sufficient to impair or prevent the gelation (or to impair the physical properties of the resultant gels. The present inventors have found that substantially reducing the amount of contaminating proteins in the hemicellulosic material prior to gelation makes possible the production of gelling hemicellulose from a wider range of bran sources (including those previously thought as intractable or unsuitable as starting materials) than has hitherto been possible, and significantly improves the quality of the resultant gels.

This novel finding is particularly surprising in the light of the critical role thought to be played by proteins in the gelling process (see e.g. Hoseney and Fabuion (1981), Cereal Chem., 58: 421, referred to infra).

Thus, according to the present invention there is provided a process for the production of a gelling hemicellulose from a bran containing interfering levels of contaminating protein, the process comprising the steps of extracting hemicellulose from the bran and removing the contaminating protein before and/or after extraction.

As used herein, the term "interfering levels of contaminating protein" refers to concentrations of bran-associated proteins which are sufficient to impair the quality of gels produced by oxidative gelation of hemicellulose extracts prepared therefrom (or prevent or impair gelation of such hemicellulose extracts). In general, protein concentrations of 10% w/w or greater (with respect to the total weight of the bran starting material) are at interfacing levels (within the terms of the definition set out above). The contaminating protein is usually endogenous to the bran (i.e. carried over from the milling process), and often comprises or consists of endosperm material. Examples of brans which contain interfering levels of contaminating proteins include many wheat brans and some European corn brans. In many cases, brans which contain interfering levels of contaminating proteins are those which are associated with significant amounts of residual endosperm material.

The contaminating protein need not be removed entirely, but merely to a level sufficient to improve the gelling characteristics or gel quality of the gels ultimately produced. The level of contaminating protein is preferably reduced to a level sufficient to restore or improve the gel (or extract gelling) properties. For example, the contaminating protein concentration may be reduced to below about 15%, 14%, 13%, 12%, 11%, 10%, 9%, 8%, 7%, 6%, 5%, 4%, 3%, 2%, or 1%.

The contaminating protein may be removed from the bran by any convenient method, and a wide variety of suitable techniques are known to those skilled in the art. The protein may be removed from the bran itself prior to extraction, from the hemicellulosic bran extract, or from both.

Conveniently, protein removal may include classifying, washing and/or sieving the bran. In such processes, contaminating starch may be removed together with the contaminating protein. In such (dry) techniques, contaminating protein may be removed from the bran as endosperm fragments on the basis of size (e.g. by air classifying, washing or sieving the bran). Preferably, the bran is sieved through a mesh of 0–250 $\mu$m, 250–260 $\mu$m, 600–1000 $\mu$m and/or grater than 1000 $\mu$m. The sieving may be followed by air classification of the sieved bran to remove endosperm fragments, e.g. through a mesh of less than 600 $\mu$m (e.g. less than 250 $\mu$m. Alternatively, or in addition, contaminating protein may be removed from the bran by washing, for example with hot water or acid (e.g. at a pH of 3–6, e.g. about 5).

Contaminating protein may also be removed from the bran and/or the hemicellulose extract by treatment with a protease. This technique can be applied as the sole protein removal step, or used in any combination with any other method, such as those disclosed herein. In such embodiments, a bran residue may be recovered from protease treatment and the residue washed with hot water or acid (e.g. at a pH of 3–6, e.g. about 5). The protease treatment is conducted for a period of time sufficient to improve the gelling characteristics and/or ultimate quality of the resultant gels, and for example may be conducted for about 10–20 min (e.g. about 1 hr), for example at 30–80° C., (e.g. about 50° C.).

Alternatively, or in addition, contaminating protein may be removed from the hemicellulose extract by heat treating the hemicellulose extract to form a proteinaceous precipitate (for example at 70–100° C., e.g. about 35–100° C., optionally for 5–60 min, e.g. about 20 min). Preferably, such heat treatment comprises the steps heat treating the hemicellulose extract to form a proteinaceous precipitate; removing the precipitate to produce a hemicellulose-enriched supernatant and then recovering gelling hemicellulose from the enriched supernatant.

Other techniques which may be used according to the present invention (alone or in combination with other protein removal steps) include precipitation (e.g. isoelectric precipitation), filtration (e.g. ultrafiltration and/or filtration on vega clay), chromatography (e.g. silica hydrogel and/or ion exchange chromatography) and/or alcohol (e.g. IMS) precipitation, for example with up to 30% v/v alcohol. Particularly preferred is the use of isoelectric precipitation of the hemicellulose extract at a pH of between 2 and 5 (e.g about 4).

In preferred embodiments, the process comprises the steps of: (a) treating the bran with a protease to yield a bran digest (e.g. under the conditions defined above); (b) extracting hemicellulose from the digest of step (a); (c) heat treating the hemicellulose extract of step (b) to form a proteinaceous precipitate; (d) removing the precipitate of step (c) to produce a hemicellulose-enriched supernatant; (e) recovering gelling hemicellulose from the enriched supernatant of step (d). The bran residue may be recovered after protease treatment and the residue washed with hot water or acid (e.g. at a pH of 3–6, e.g. about 5).

Preferably, the hemicellulose extraction is an alkaline extraction, for example a mild alkaline extraction. For example, the alkaline extraction may be carried out under conditions which do not substantially deferulate polysaccharides (e.g. arabinoxylan) in the hemicellulose. Particularly preferred are alkali extractions conducted with alkali metal hydroxides, such as sodium hydroxide, calcium hydroxide and potassium hydroxide. Calcium hydroxide is particularly advantageous where clear gels are required, because it can be readily precipitated out. The hydroxide is preferably used at about 1–15%, though the optimum amount can be readily determined by routine trial and error by those skilled in the art and depends inter alia on the particular bran source used. For example, concentrations of about 5% are useful for many wheat brans, whereas concentrations of about 10% are preferred for maize brans. Particularly preferred for wheat brans is potassium hydroxide at about 54 w/w. The alkaline treatment is preferably carried out for about 10–120 min, for example for about 1 hr. The extraction may be conducted at 30–80° C. (e.g about 60° C.).

Preferably, the process further comprises the step of recovering gelling hemicellulose by alcohol precipitation, optionally followed by drying.

A particularly preferred process is shown in schematic form in FIG. 1. Here, "BWB" and "FWB" are abbreviations for broad wheat bran and fine wheat bran, respectively. The "WIP" and "WSP" processes are abbreviations for the water insoluble and water soluble pentosan co-product process respectively. The arrow to the protein deposit shown ("PD") is another important co-product route. The process shown in this figure may further comprise "fine finishing" steps after final trituration in IMS. Such fine finishing may include, for example, starch removal (e.g. by processes comprising centrifugation).

The gelling hemicellulose may comprise a pentosan, e.g. a water soluble or alkali soluble pentosan fraction. Particularly preferred is arabinoxylan, for example arabinoxylan ferulate. For many applications, the gelling hemicellulose will consist of (or consist essentially of) arabinoxylan ferulate.

The bran may be any bran in which the level of contaminating protein is sufficiently high so as to interfere with oxidative gelation of hemicellulose extracts prepared therefrom (e.g. by alkaline extraction as described, for example, infra). The brain is preferably a cereal bran, for example European corn bran (e.g. German corn bran) or wheat bran.

In another aspect, the invention contemplates a process for the production of a hemicellulose gel comprising the steps of: (a) preparing a gelling hemicellulose according to a process as defined in any one of claims 1–28; and then (b) oxidatively gelling the hemicellulose obtained in step (a) to yield a hemicellulose gel.

The processes of the invention yield useful and important co-products. These include bran derived starch, protein, starch-protein mixtures and the unextracted residue left after extraction of the gelling hemicelluloses. This latter material can be further processed (as described infra) to yield a variety of soluble and insoluble pentosan extracts having a wide range of uses in the food industry, the pharmaceutical industry and more generally (e.g. as adhesives or sealants). The protein produced as a by product of the invention has been found to exhibit excellent organoleptic qualities (particularly when digested to varying extents with a protease). Moreover, it has an excellent amino acid profile and is particularly nutritious, being superior to gluten in many respects. Without wishing to be bound by any theory, it is thought that the protein co-products of the invention comprise non-storage protein derived from the endosperm of the plant from which the bran was produced.

Thus, the processes of the invention preferably further comprise the step of recovering the contaminating protein removed from the bran (e.g. in digested form), and may also further comprise the step of recovering contaminating starch removed from the bran (e.g. in admixture with the contaminating protein).

In another aspect, the invention relates to a process for preparing a protein or a mixture of starch and protein comprising the steps of: (a) providing a bran (for example a bran as defined in claim 28); (b) removing protein (and optionally starch) from the bran by processing as defined in any one of claims 1–28; and (c) recovering the protein (optionally in admixture with starch) removed in step (b); and optionally (d) drying or concentrating the protein (and optionally the starch) recovered in step (c).

The invention also contemplates various products comprising the co-products of the invention. Such co-products may, for example, be formulated as a food, food ingredient, food base, food additive or functional feed ingredient comprising the protein co-product of the invention.

The protein co-product may be formulated as: (a) an emulsifier; (b) a binder; (c) a whipping agent; (d) a soya analogue; (e) a milk analogue; (f) a protein isolate or concentrate; (g) a flavouring agent; (h) a dehydrated beverage; (i) a roux or roux blanc; (j) a moisture barrier. For some applications, it is preferred that the protein co-product be at least partially digested, conveniently by the protease treatment applied to the bran or hemicellulose extract in the main product pathway.

The gelling hemicellulose may conveniently be provided in the form of a powder, for example a substantially anhydrous power and optionally a dispersant (e.g. glucose or maltodextrin). In this form it may further comprise an oxidase, oxidase substrate (e.g. glucose) and optionally peroxidase supplements, so that the material is self-gelling on the addition of water.

The gelling hemicellulose of the invention may also be provided in the form of an aqueous solution, which is advantageously substantially oxygen free. Such materials may also comprise an oxidase, oxidase substrate (e.g. glucose) and optionally peroxidase supplements, and so also be self-gelling on exposure to oxygen.

The invention also contemplates a gel or viscous medium comprising the gelling hemicellulose of the invention which has been oxidatively gelled. The gelling hemicellulose may comprise (or consist of) cross linked arabinoxylan.

The invention also contemplates a pharmaceutical or cosmetic preparation or medical device comprising the hemicellulosic materials of the invention. The preparation or device may for example be selected from: a wound plug, wound dressing, wound debriding system, controlled release device, an encapsulated medicament or drug, a lotion, cream, suppository, pessary, spray, artificial skin, protective membrane, a neutraceutical, prosthetic, orthopaedic, ocular insert, injectant, lubricant or cell implant matrix. In such embodiments the material, gel or viscous medium of the invention may further comprising an antibiotic, electrolyte, cell, tissue, cell extract, pigment, dye, radioisotope, label, imaging agent, enzyme, co-factor, hormone, cytokine, vaccine, growth factor, protein (e.g. a therapeutic protein), allergen, hapten or antigen (for e.g. sensitivity testing), antibody, oil analgesic and/or antiinflammatory agent (e.g. NSAID).

The invention also covers the materials of the invention for use in therapy, surgery, prophylaxis or diagnosis, for example in the treatment of surface (e.g. skin or membrane lesions, e.g. burns, abrasions or ulcers).

In a particularly preferred embodiment, the invention contemplates a wound dressing comprising the material of the invention, for example in the form of a spray. Such would dressings are particularly useful for the treatment of burns, where their great moisture retaining properties help to prevent the wound drying out. Particularly preferred for such application is the self-gelling liquid of the invention which gels on contact with oxygen in the air. Such compositions can be provided in the form of oxygen-free liquids in airtight containers which can be sprayed onto the skin, whereupon the liquid gels after exposure to the air. Such composition may advantageously be formulated so as to produce a slight excess of hydrogen peroxide on exposure to oxygen, so that a sterilizing, antibacterial, bacteriostatic and/or cleansing effect is obtained which helps promote healing.

The invention also contemplates water absorbant nappies, diapers, incontinence pads, sanitary towels, tampons and panty liners comprising the materials and gels of the invention, as well as domestic and industrial cleaning or liquid (e.g. water) recovery operations (e.g. in the oil industry).

Alternatively, the gels of the invention can be provided in the form of hydrated or dehydrated sheets or pellicles for application to various internal or external surfaces of the body, for example during abdominal surgery to prevent adhesions. Other embodiments include enzyme immobilizing systems and brewing adjuncts. Also contemplated is a bread improver comprising the material, gel or viscous medium of the invention.

The invention also covers a foodstuff, dietary fibre source, food ingredient, additive, lubricant, supplement or food dressing comprising the material, gel or viscous medium of the invention. Such products are preferably selected from crumb, alginate replacer, cottage cheeses, aerosol toppings, frozen yoghurts, milk shakes, ice cream, low calorie products such as dressings and jellies, batters, cake mixes, frozen chips, binders, gravies, pastas, noodles, doughs, pizza toppings, sauces, mayonnaise, jam, preserve, pickles, relish, fruit drinks, syrups, toppings and confectionary (e.g. soft centres), petfood (wherein the gel e.g. acts as a binder), a flavour delivery agent, a canning gel, fat replacer (e.g. comprising macerated gel of any one of claims ), a coating, a glaze, a bait, a binder in meat and meat analogue products (for example vegetarian products), a gelatin replacer or dairy product or ingredient (e.g. a yoghurt supplement). When used as a fat replacer the gel of the invention is preferably macerated to optimize its mouthfeel and fat mimetic properties.

The invention also finds application in the extraction of gelling hemicelluloses from sources other than bran which may contain interfering levels of contaminating protein. The invention may be used to extract essentially any hemicellulose (within the definition set out earlier). In particular, the hemicellulose may be an arabinoxylan, heteroxylan or pectin. In addition, the hemicellulose for use in the processes of the invention may be a synthetic hemicellulose (i.e. a structural analogue of a naturally-occurring hemicellulose synthesized in vitro by any chemical/enzyme synthesis or modification). Arabinoxylans, heteroxylans and pectins may also be used. Of the arabinoxylans, particularly preferred are AXFA, AXF, AXA and AX.

Also suitable for use in the invention are pectins, including the true pectins, simple pectins, complex pectins, mesocomplex pectins and gelling pectins (e.g those obtainable from representatives of the plant family Chenopodiaceae, which include beets, (e.g. sugar beet), spinach and mangelwurrels). Particularly preferred is sugar beet pectin (for example in the form of sugar beet pulp). Also useful in the invention are treated pectins (as hereinbefore defined).

Examples of sources other than bran which may be used as starting materials according to the invention include any non-cellulosic, non-starch plant polysaccharides. Thus, the processes of the invention find application in the processing inter alia of pentosans, pectins and gums. Suitable starting materials containing hemicellulose for use in the processes of the invention typically include plant material of various kinds and any part or component thereof.

Plant materials useful as a starting material in the invention include the leaves and stalks of woody and nonwoody plants (particularly monocotyledonous plants), and grassy species of the family Gramineae. Particularly preferred are gramineous agricultural residues, i.e. the portions of grain-bearing grassy plants which remain after harvesting the seed. Such residues include straws (e.g. wheat, oat, rice, barley, rye, buckwheat and flax straws), corn stalks, corn cobs and corn husks.

Other suitable starting materials include grasses, such as prairie grasses, gamagrass and foxtail. Other suitable sources include dicotyledonous plants such as woody dicots (e.g. trees and shrubs) as well as leguminous plants.

Another preferred source are fruits, roots and tubers (used herein in the botanical sense). The term "fruit" includes the ripened plant ovary (or group thereof) containing the seeds, together with any adjacent parts that may be refused with it at maturity. The term "fruit" also embraces simple dry fruits (follicles, legumes, capsules, achenes, grains, samaras and nuts (including chestnuts, water chestnuts, horsechestnuts etc.)), simple fleshy fruits (berries, drupes, false berries and pomes), aggregate fruits and multiple fruits. The term "fruit" is also intended to embrace any residual or modified leaf and flower parts which contain or are attached to the fruit (such as a bract). Encompassed within this meaning of fruit are cereal grains and other seeds. Also contemplated for use as starting material are fruit components, including bran, seed hulls and culms, including malt culms. "Bran" is a component of cereals and is defined as a fraction obtained during the processing of cereal grain seeds and comprises the lignocellulosic seed coat as separate from the flour or meal. Other suitable component parts suitable as starting materials include flours and meals (particularly cereal flours and meals, and including nonwoody seed hulls, such as the bracts of oats and rice).

The term "root" is intended to define the usually underground portion of a plant body that functions as an organ of absorption, aeration and/or food storage or as a means of anchorage or support. It differs from the stem in lacking nodes, buds and leaves. The term "tuber" is defined as a much enlarged portion of subterranian stem (stolon) provided with buds on the sides and tips.

Preferred lignocellulosic starting materials include waste stream components from commercial processing of crop materials such as various beets and pulps thereof (including sugar beet pulp), citrus fruit pulp, wood pulp, fruit rinds, nonwoody seed hulls and cereal bran. Suitable cereal sources include maize, barley, wheat, oats, rice, other sources include pulses (e.g. soya), legumes and fruit.

Other suitable starting materials include pollen, bark, wood shavings, aquatic plants, marine plants (including algae), exudates, cultured tissue, synthetic gums, pectins and mucilages.

Particularly preferred as a starting material is testaceous plant material, for example waste testaceous plant material (preferably containing at least about 20% of arabinoxylan and/or glucoronoarabinoxylan).

The starting material may be treated directly in its field-harvested state or (more usually) subject to some form of pre-processing. Typical pre-processing steps include chopping, grinding, cleaning, washing, screening, sieving etc.

APPLICATIONS

The hemicellulose products (i.e. the gels, dehydrated gels, rehydrated dehydrated gels, non-gelling hemicelluloses, gelling (but ungelled) hemicelluloses and viscous liquids of the invention find a variety of applications various therapeutic, surgical, prophylactic, diagnostic and cosmetic (e.g. skin care) applications.

For example, the aforementioned materials may be formulated as a pharmaceutical or cosmetic preparation or medical device, for example selected from: a wound plug, wound dressing, wound debriding system, controlled release device, an encapsulated medicament or drug, a lotion, cream (e.g. face cream), suppository, pessary, spray, artificial skin, protective membrane, a neutraceutical, prosthetic, orthopaedic, ocular insert, injectant, lubricant or cell implant matrix. The non-gelling gelling and gelled hemicelluloses (e.g AX, AXF and gelled AXF) are particularly useful as agents which maintain the integrity of the gut wall lining, and as agents for coating the luminal wall of the gastrointestinal tract. They may therefore fins particular application in animal feeds and in the treatment of gastrointestinal disorders.

In such embodiments the material, gel or viscous medium of the invention may further comprising an antibiotic, electrolyte, cell, tissue, cell extract, pigment, dye, radioisotope, label, imaging agent, enzyme co-factor, hormone, cytokine, vaccine, growth factor, protein (e.g. a therapeutic protein), allergen, hapten or antigen (for e.g. sensitivity testing), antibody oil, analgesic and/or antiinflammatory agent (e.g. NSAID).

Thus, the above-listed materials find application in therapy, surgery, prophylaxis or diagnosis, for example in the treatment of surface (e.g. skin or membrane lesions, e.g. burns, abrasions or ulcers). In a particularly preferred embodiment, the invention contemplates a wound dressing comprising the above listed materials of the invention, for example in the form of a spray. Such wound dressings are particularly useful for the treatment of burns, where their great moisture retaining properties help to prevent the wound drying out.

Particularly preferred for such application is a self-gelling liquid comprising gelling hemicellulose supplemented with glucose and peroxidase and/or oxidase enzymes which gels on contact with oxygen in the air. Such compositions can be provided in the form of oxygen-free liquids in airtight containers which can be sprayed onto the skin, whereupon the liquid gels after exposure to the air. Such composition may advantageously be formulated so as to produce a slight excess of hydrogen peroxide on exposure to oxygen, so that a sterilizing, antibacterial, bacteriostatic and/or cleaning effect is obtained which helps promote healing.

The invention also contemplates water absorbent nappies, diapers, incontinence pads, sanitary towels, tampons and panty liners comprising the above-listed materials, as well as domestic and industrial cleaning or liquid (e.g. water) recovery operations (e.g. in the oil industry).

Alternatively, the gels of the invention can be provided in the form of hydrated or dehydrated sheets or pellicles for application to various internal or external surfaces of the body, for example during abdominal surgery to prevent adhesions.

Other applications include enzyme immobilizing systems, brewing adjuncts and bread improvers.

The materials listed above also find application as a foodstuff, dietary fibre source, food ingredient, additive, lubricant, supplement or food dressing. Such products are preferably selected from crumb, alginate replacer, cottage cheeses, aerosol toppings, frozen yoghurts, milk shakes, ice cream, low calorie products such as dressings and jellies, batters, cake mixes, frozen chips, binders, gravies, pastas, noodles, doughs, pizza toppings, sauces, mayonnaise, jam, preserve, pickles, relish, fruit drinks, a clouding agent in drinks, syrups, toppings and confectionary (e.g soft centres), petfood (wherein the gel e.g. acts as a binder), a flavour delivery agent, a canning gel, fat replacer (e.g. comprising macerated gel), a coating, a glaze, a bait, a binder in meat and meat analogue products (for example vegetarian products), an edible adhesive, a gelatin replacer or dairy product or ingredient (e.g. a yoghurt supplement).

When used as a fat replacer the gel of the invention is preferably macerated to optimize its mouthfeel and fat mimetic properties.

The ungelled gellable hemicelluloses and the non-gelling hemicelluloses find particular utility as biodegradable gums and adhesives, e.g for use in the paper and packaging industries.

Nongelling hemicelluloses (for example, AX) also find particular application as stabilizers, thickeners and gelatin replacers. They have excellent mouthfeel and texture when used in, for example, mousses and other dairy products.

The ungelled (but gellable) hemicelluloses (e.g. AXF) find particular application as clouding agents (e.g in drinks), as film forming agents (e.g. in moisture barriers), glazes, edible adhesives and other functional food ingredients.

The cellulose fibre is usually bleached prior to use. It has high water holding capacity, and dispersions may be sheared to produce highly viscous pastes. Particularly preferred applications for this (co) products include dressings (e.g as a modified starch replacer), yogurts and coatings (and especially batters), where it may act as a crisping agent.

The protein (co) products of the invention have been found to exhibit excellent organoleptic qualities (particularly when digested to varying extents with a protease). Moreover, they have an excellent amino acid profile and are particularly nutritious, being superior to gluten in many respects. Without wishing to be bound by any theory, it is thought that the protein (co) products of the invention derived from starting materials comprising bran comprise non-storage protein derived from the endosperm of the plant from which the bran was produced.

The protein co-product may be formulated as: (a) a emulsifier; (b) a binder; (c) a whipping agent; (d) a soya analogue; (e) a milk analogue; (f) a protein isolate or concentrate; (g) a flavouring agent; (h) a dehydrated beverage; (i) a roux or roux blanc; (j) a moisture barrier.

For some applications, it is preferred that the protein co-product be at least partially digested, conveniently by the protease treatment applied to the starting material (e.g. bran) or hemicellulose extract in the main process stream.

The various other co-products of the invention (including the β-glucan, starch, protein, cellulose, phenolic extracts, lignin, wax, cutin and/or suberin) find application as foods, food ingredients, food bases, food additives or functional food ingredients. They also find application in various forms of therapy (particularly wound healing).

Particularly preferred in the latter respect are the phenolic extracts of the invention, which also find particular utility as flavouring agents (e.g vanilla flavourings).

Some of the phenolic extracts and/or waxes, cutins and/or suberins find particular utility as pesticides or crop protection agents.

BRIEF DESCRIPTION OF THE DRAWING

FIG. 1 is a diagram that shows the process of extracting supergel from wheat bran.

The invention will now be illustrated in more detail by reference to examples, which are for illustrative purposes only and do not limit the scope of the invention.

EXAMPLE 1

101 of sodium acetate buffer (pH5, 0.02 M) were pre-equilibrated at 50° C. and 10 ml of liquid protease (Profix™) was added.

1 kg of fine wheat bran was added to this enzyme solution, and the suspension mixed vigorously for 60 min, maintaining the temperature at 50° C. The bran residue was then washed over a 200 $\mu$m sieve, and rinsed with 31 of hot water. the washings were discarded and the bran residue recovered.

The washed bran residue was then resuspended in 51 of sodium acetate buffer (pH5, 0.02 M) at 60° C. and mixed continuously, maintaining the temperature at 60° C. 25 g of KOH pellets were then added, and mixing continued for 60 min at 60° C.

After 60 min, the mixture was neutralized to pH7 with acetic acid and filtered to recover liquid. The mixture was then left to stand while a precipitate forms. Alternatively, the mixture may be centrifuged. A clear, dark golden brown supernatant is recovered.

The pH of the supernatant is then brought to pH 4.8 with acetic acid and 1.5 volumes of IMS added. Further acetic acid is added to maintain the pH at 4.8

Polysaccharides are then recovered by centrifugation and solvent exchange, and the polysaccharides then dried with acetone. Alternatively, any other suitable method of polysaccharide extraction can be employed.

The gelling hemicellulose produced by this method yielded firm, clear gels at low concentrations.

EXAMPLE 2

The procedure described in Example 1 was repeated, except that after recovery of polysaccharides, the extract is heated to 50° C. (if necessary to disperse) and then held at a temperature of 95–100° C. for 20 min. This denatures residual proteins which are removed by centrifugation (or any other suitable separation method).

The gelling hemicellulose produced by this method yielded firm, clear gels at low concentrations.

EXAMPLE 3

The procedure described in Example 1 was repeated, except that immediately before recovery of polysaccharides, the extract is heated to 50° C. (if necessary to disperse) and then held at a temperature of 95–100° C. for 20 min. This denatures residual proteins which are removed by centrifugation (or any other suitable separation method).

The gelling hemicellulose produced by this method yielded firm, clear gels at low concentrations.

EXAMPLE 4

Oven dried European corn bran was size fractionated by mechanical agitation across 1.0 mm, 600 $\mu$m, and 250 $\mu$m sieves. The distribution of dry matter in each size class was as follows:

| (a) | 0–250 $\mu$m | 26% |
|---|---|---|
| (b) | 251–600 $\mu$m | 18% |
| (c) | 601 $\mu$m–1.0 mm | 29% |
| (d) | >1.0 mm | 27% |

Without wishing to be bound by theory, the smallest size fraction (a) was thought to be starch.

The largest two fractions (c and d) representing 56% of the starting material were then further air classified, which separated solid particles of maize endosperm from the bran particles. Clean bran particles represented 85% of the sieved fractions (c and d), i.e. 48% of the starting material.

The clean bran particles were then size reduced until then passed a 250 $\mu$m sieve, and this cleaned bran then used for extraction.

Extraction was carried out with a 10% w/v dispersion of bran and 10% w/w KOH: clean bran (1% w/v KOH). The extraction was carried out with mixing at 70° C. for 1 hour after which the suspension was neutralized to pH7 with acetic acid. An aliquot of this crude liquid extract was found to gel in the presence of peroxide/peroxidase to give an opaque red/brown coloured gel.

The extract was left for about 30 min and the liquid and solid phases separated using Whatman No. 40 filter paper. The liquid phase was recovered, the pH adjusted to 4.8 and 1.5 volumes IMS added to precipitate polysaccharides. The pH was then readjusted to 5 and samples left for 1 hour.

Solid AXF was recovered by solvent exchange with IMS, finally drying with acetone at 70° C. The dried product, when formulated as a 1% solution at pH7, formed a clear gel on the addition of peroxide/peroxidase.

EXAMPLE 5

Broad wheat bran was sieved to a 500–700 $\mu$m mesh size to remove starch. 300 g of the sieved bran was added to 3500 ml hot (70° C.) 0.025 M sodium acetate-acetic acid buffer (pH5). 15 g KOH (5% w/w based on bran) was added and the suspension stirred for 60 min at 70° C. The extract was neutralized to pH7 with glacial acetic acid, filtered through muslin gauze and the filter cake washed with 400 ml hot (70° C.) water.

The filtrate was then adjusted to pH 4 with concentrated HCl and cooled to 4° C. for 2 h and then left at room temperature overnight during which a protein deposit settled out. The suspension was centrifuged (4000 rpm, 30 min, 4° C.). The pellets (protein deposits) were frozen and freeze dried.

The supernatant was adjusted to pH 4.87 with concentrated HCl or 40% w/v KOH and arabinoxylan precipitated with 1.5 volumes of 99% IMS. The pH was then readjusted to pH 4.87 with concentrated HCl. Precipitates were triturated three times with 99% IMS, filtered through Propex™ 93 K and vacuum dried.

A 2% solution of the product in water formed a clear, non synerising gel on the addition of peroxide/peroxidase. Similar gels were obtained after centrifugation of the 2% solution (4000 rpm for 30 min), though these gels were lower in starch than those produced from non-centrifuged solutions.

EXAMPLE 6

Fine wheat bran was sieved to a 500–1000 $\mu$m mesh size to remove starch. 300 g of the sieved bran was added to 3000 ml hot (70° C.) 0.025 M sodium acetate-acetic acid buffer (pH5). 15 g KOH (5% w/w based on bran) was added and the suspension stirred for 60 min at 70° C. The extract was neutralized to pH7 with glacial acetic acid, filtered through muslin gauze and the filter cake washed with 400 ml hot (70° C.) water.

The filtrate was then adjusted to pH 4 with concentrated HCl and cooled to 4° C. for 1 h and then left at room temperature overnight during which a protein deposit settled out. The suspension was centrifuged (4000 rpm, 30 min, 4° C.). The pellets (protein deposits) were frozen and freeze dried.

The supernatant was adjusted to pH 4.87 with concentrated HCl or 40% w/v KOH and arabinoxylan precipitated with 1.5 volumes of 99% IMS. The pH was then readjusted at pH 4.87 with concentrated HCl. Precipitates were triturated three times with 99% IMS, filtered through Propex™ 93 K and vacuum dried.

A 2% solution of the product in water formed a clear, non synerising gel on the addition of peroxide/peroxidase. Similar gels were obtained after centrifugation of the 2% solution (4000 rpm, for 30 min), though these gels were lower in starch than those produced from non-centrifuged solutions.

EXAMPLE 7

Broad wheat bran was sieved to a 500–1700 $\mu$m mesh size to remove starch. 9.78 kg of the sieved bran was added to 115 l hot (70° C.) 0.025 m sodium acetate-acetic acid buffer (pH5). 0.489 kg KOH (5% w/w based on bran) was added and the suspension stirred for 60 min at 70° C. The extract was neutralized to pH7 with glacial acetic acid (0.175 l), filtered through muslin gauze and the filter cake washed with 10 l hot (70° C.) water.

The filtrate (109 l) was then adjusted to pH 4 with concentrated HCl (0.9 l) and left at room temperature overnight during which a protein deposit settled out. The supernatant (31 l) was decanted and the remaining liquor plus protein deposit (70 l) centrifuged (4000 rpm, 30 min). This supernatant was combined with the original (31 l) to give a total volume of 94 l. The pellet (protein deposit) was frozen and freeze dried.

The supernatant was adjusted to pH 4.87 with 40% w/v KOH and arabinoxylan precipitated with 1.5 volumes of 99% IMS. The pH was then readjusted to pH 4.87 with concentrated HCl. Precipitates were triturated three times with 99% IMS, filtered through Propex™ 93 K and vacuum dried.

A 2% solution of the product in water formed a clear, non synerising gel on the addition of peroxide/peroxidase.

EXAMPLE 8

The filter cake from the above extraction of Example 7 was suspended in 115 l hot (70° C.) water. 1.725 kg KOH (1.5% w/v) was added and the suspension stirred for 1 h at 70° C. The extract was filtered in 25 l aliquots through two thicknesses of muslin gauze and the filter cake washed with hot (70° C.) water to yield filtrates and washings which were processed further (see Example 9, below).

The washed solids were resuspended in cold water and made up to a total volume of 90 l with the same. 15 l 35% v/v $H_2O_2$ was added (equivalent to a final concentration of 13% v/v after pH adjustment) and the pH adjusted to 12.2 with 40% w/v KOH (10 l) and the suspension stirred for 2 h at room temperature after which 0.5 volumes 90% IMS was added and the reaction left unstirred at room temperature overnight. The suspension was adjusted to pH 9 with concentrated HCl (9 l) and 25 l aliquots were filtered through two thicknesses of muslin gauze. Each cake was washed three times with 5 l hot (70° C.) water, the cakes combined, resuspended in hot (70° C.) water and made up to 75 l total volume with the same. The suspension was acidified to pH 5 with concentrated HCl (0.05 l), filtered through two thicknesses of muslin gauze and the solids washed twice with 5 l hot (70° C.) water then once with 5 l cold water. The washed product was frozen and freeze dried as a by product useful e.g as a functional food ingredient.

EXAMPLE 9

The filtrates and washings from Example 8 was adjusted to pH 5 with concentrated HCl. A product was precipitated by adding 1.5 volumes 90% IMS. The precipitate was triturated twice with 90% IMS and once with 99% IMS, filtered through Propex™ 93 K and vacuum dried. The product was useful e.g. as an adhesive.

EXAMPLE 10

Fine wheat bran was sieved to a 500–1000 $\mu$m mesh size to remove starch. 11.5 kg of the sieved bran was added to 115 l hot (70° C.) 0.025 M sodium acetate-acetic acid buffer (pH5). 0.575 kg KOH (5% w/w based on bran) was added and the suspension stirred for 60 min at 70° C. The extract was neutralized to pH7 with facial acetic acid (0.22 l), filtered through muslin gauze and the filter cake washed with 10 l hot (70° C. ) water.

The filtrate (106 l) was then adjusted to pH 4 with concentrated HCl (1.0 l) and left at room temperature overnight during which a protein deposit settled out. The supernatant was too cloudy to decant, so the whole was centrifuged (4000 rpm, 30 min). The pellet (protein deposit) was frozen and freeze dried.

The supernatant was adjusted to pH 4.87 with 40% w/v KOH and arabinoxylan precipitated with 1. 5volumes of 99% IMS. The pH was then readjusted to pH 4.87 with concentrated HCl. Precipitates were triturated three times with 99% IMS, filtered through Propex1υ 93 K and vacuum dried.

A 2% solution of the product in water formed a clear, non synerising gel on the addition of peroxide/peroxidase.

EXAMPLE 11

The filter cake take from the above extraction of Example 10 was suspended in 115 l hot (70° C.) water. 1.725 kg KOH (1.5% w/v) was added and the suspension stirred for 1 h at 70° C. The extract was filtered in 25 l aliquots through two thicknesses of muslin gauze and the filter cake washed with hot (70° C.) water to yield filtrates and washings which were processed further (see Example 12, below).

The washed solids were resuspended in cold water and made up to a total volume of 100 l with the same. 3.45 l 35% v/v $H_2O_2$ was added (equivalent to a final concentration of 3% v/v after pH adjustment) and the pH adjusted to 12.2 with 40% w/v KOH and the total volume made up to 115 l with hot (70° C.) water. The suspension stirred for 2 h at 70° C. then left unstirred at room temperature overnight. 25 l aliquots were filtered through two thicknesses of muslin gauze. Each cake was washed three times with hot (70° C.) water, the cakes combined, resuspended in hot (70° C.) water and made up to 75 l total volume with the same. The suspension was acidified to pH 5 with concentrated HCl, filtered through two thicknesses of muslin gauze and the solids washed twice with 5 l hot (70° C.) water then once with 5 l cold water. The washed product was frozen and freeze dried as a by product useful e.g. as a functional food ingredient (e.g. as a food thickener or fat replacer.

EXAMPLE 12

The filtrates and washings from Example 11 was adjusted to pH 5 with concentrated HCl. A product was precipitated by adding 1.5 volume 90% IMS. The precipitate was triturated twice with 90% IMS and once with 99% IMS, filtered through Propex™ 93 K and vacuum dried. The product is useful e.g as an adhesive.

EXAMPLE 13

German corn bran was sieved to remove starch and ground in a blender. 40 g of the sieved bran was suspended in 400 ml hot (70° C.) 0.025 M sodium acetate-acetic acid buffer (pH5) 3.6 k KOH (9% w/w based on bran) was added and the suspension stirred for 60 min at 70° C. The extract was neutralized to pH7 with glacial acetic acid and filtered through a muslin gauze.

The filtrate was then adjusted to pH 4.87 with glacial acetic acid and the insolubles allowed to settle overnight at room temperature and then centrifuged (4000 rpm, 30 min). The pellets (protein deposits) were frozen and freeze dried.

The supernatant was adjusted to pH 4.87 and arabinoxylan precipitated with 1.5 volumes of 99% IMS. Glacial acetic acid was added to the IMS liquor to a final molarity of 0.2 M. The precipitate (thought to comprise arabinoxylan ferulate) was triturated three times with 99% IMS, filtered through Propex™ 93 K and vacuum dried.

A 2% solution of product in water formed a firm, clear, non synerising gel on the addition of peroxide/peroxidase.

What is claimed is:

1. A process for the production of a gelling hemicellulose from a bran which contains interfering levels of contaminating protein, the process comprising the steps of:

a) treating a bran with a protease to yield a bran digest;
   b) extracting hemicellulose from the digest of step (a);
   c) heat treating the hemicellulose extract of step (b) to form a proteinaceous precipitate;
   d) removing the precipitate of step (c) to produce a hemicellulose-enriched supernatant; and
   e) recovering gelling hemicellulose from the enriched supernatant of step (d).

2. The process of claim 1, wherein a bran residue is recovered after protease treatment and the residue washed with hot water or acid.

* * * * *